United States Patent [19]

Razzano

[11] Patent Number: 5,739,370

[45] Date of Patent: Apr. 14, 1998

[54] PROCESS THE PRODUCTION OF OCTAPHENYLCYCLOTETRASILOXANE

[75] Inventor: John S. Razzano, Cohoes, N.Y.

[73] Assignee: General Electric Company, Waterford, N.Y.

[21] Appl. No.: 825,863

[22] Filed: Apr. 29, 1997

[51] Int. Cl.$^6$ .................................................. C07F 7/08
[52] U.S. Cl. ............................................................ 556/461
[58] Field of Search ............................................... 556/461

[56] References Cited

U.S. PATENT DOCUMENTS

| | | |
|---|---|---|
| 3,842,110 | 10/1974 | Razzano . |
| 4,079,070 | 3/1978 | Maass et al. . |
| 4,382,145 | 5/1983 | Yeboah ........................ 556/461 X |
| 4,383,145 | 5/1983 | Yeboah ........................ 556/461 X |
| 4,390,713 | 6/1983 | Martin . |
| 4,507,455 | 3/1985 | Tangney et al. . |
| 5,302,659 | 4/1994 | Bindl et al. . |
| 5,399,652 | 3/1995 | Bindl et al. . |
| 5,545,837 | 8/1996 | Kobayashi ........................ 556/461 X |

OTHER PUBLICATIONS

"Product–Specific Methods of Syntheses of Hexaphenylcyclotrisiloxane and Octaphenylcyclotetrasiloxane — Monomers of Phenyisilicons", Mei–Hui Yang, Journal of the Chinese Chemical Society, 1995, 42 923–928.

*Primary Examiner*—Paul F. Shaver
*Attorney, Agent, or Firm*—Kenneth S. Wheelock

[57] ABSTRACT

A base catalyzed hydrolysis of dialkoxydiphenylsilanes or dialkoxymethylphenylsilanes in a solvent or solvent mixture wherein dialkoxydiphenylsilanes or dialkoxymethylphenylsilanes are soluble but in which octaphenylcyclotetrasiloxane or tetramethyltetraphenyl-cyclotetrasiloxane is sparingly soluble or insoluble provides for a process to prepare octaphenylcyclotetrasiloxane or sym-tetramethyltetraphenyl-cyclotetrasiloxane in high yield.

21 Claims, No Drawings

5,739,370

PROCESS THE PRODUCTION OF OCTAPHENYLCYCLOTETRASILOXANE

FIELD OF THE INVENTION

The present invention relates to a new process for the production of octaphenylcyclotetrasiloxane. More specifically the present process relates to a process for the production of octaphenylcyclotetrasiloxane and sym-tetramethyltetraphenylcyclotetrasiloxane where the product octaphenylcyclotetrasiloxane precipitates from the reaction media.

BACKGROUND OF THE INVENTION

Octaphenylcyclotetrasiloxane is typically produced industrially by one of two processes: 1) the hydrolysis of diphenyldichlorosilane or 2) the hydrolysis of diphenyldialkoxysilanes. U.S. Pat. No. 3,842,110 ('110) discloses a process for the preparation octaphenylcyclotetrasiloxane, $((C_6H_5)_2SiO)_4$, which comprises contacting $(C_6H_5)_2Si(X)_2$ where X is a halogen with an alcohol ROH having from one to eight carbon atoms to form a reaction product having the formula: $(C_6H_5)_2Si(OR)_2$, to which is subsequently added water, a water immiscible organic solvent and an alkaline rearrangement catalyst followed by heating to between 40° and 80° C. which gives off the alcohol as a by-product and forms the desired octaphenylcyclotetrasiloxane. Generally this reaction requires refluxing for anywhere from one to six hours during the heating step. After heating, neutralizing acid is added and this step is followed by an azeotropic distillation in the presence of the water immiscible organic solvent to remove the water and alcohol. The solution is subsequently cooled to recover the octaphenylcyclotetrasiloxane. The process requires at least two moles of the alcohol per mole of the diphenyldihalogensilane for the alcoholysis reaction, between one and four moles of added water during the refluxing step and at least two moles of the water immiscible organic solvent for the azeotropic distillation. Approximately 10 to 5,000 ppm of the alkaline rearrangement catalyst is used. Yields of the desired octaphenylcyclotetrasiloxane vary from 68% to 72%. The process of U.S. Pat. No. 3,842,110 represented an improvement over a prior process utilizing diphenyl silane di-ol as a starting material which had the significant disadvantage in that the synthesis produced a mixture of condensation products, dimers, trimers and pentamers unless the pH was strictly controlled to around 7.

U.S. Pat. No. 4,079,070 ('070) discloses a one-step process for the preparation of octaphenylcyclotetrasiloxane by base catalyzed hydrolysis of a diphenyldihalogenosilane in the presence of aprotic organic solvents. The '070 patent teaches dissolving the diphenyldihalogenosilane in an organic aprotic solvent thereby forming a solution and adding that solution dropwise to an aqueous solution containing an alkali metal hydroxide. The weight ratio of the organic solution to the water solution must be at least 0.2 to 1, i.e. the water solution must be present in at least a five-fold excess by weight. Since the reaction is a base catalyzed hydrolysis, the halogen freed by the reaction must be consumed by the base, thus there is a requirement that 2 to 2.5 equivalents of base must be employed per mole of the diphenyldihalogenosilane. Thus the process of the '070 patent employs large amounts of base. While one advantage of the process is that low molecular weight cyclic siloxanes are formed almost exclusively the process of the '070 patent suffers from the significant disadvantage that large volumes of brackish by-product water are created because of the need to remove by-product salts from the product by washing with large volumes of water. Further, the product produced by the process of the '070 patent has a low melting point which is indicative of low purity.

The reaction of diphenylsilanediol to form hexaphenylcyclotrisiloxane ($P_3$) or octaphenylcyclotetrasiloxane ($P_4$) has been shown to be dependent upon the mode of catalysis employed for the cyclo-condensation reaction (Yang, M. H., Chou, C., and Lin, C. I., *J. Chinese Chem. Soc.*, 42, 923–928 (1995)). Acidic conditions favor the formation of $P_3$ and basic conditions favor the formation of $P_4$ with the strength of the acid or base increasing the yield of $P_3$ or $P_4$ respectively. The use of weak acids or bases yielded predominantly linear siloxane oligomers as the major product. While alcohols are the preferred solvent for the reaction of diphenylsilanediol to yield $P_3$ or $P_4$, ethanol for the production of $P_3$ and methanol for the production of P4, in no case was the yield of $P_4$ greater than 46% of theoretical.

SUMMARY OF THE INVENTION

The present invention thus provides for a process for the production of octaphenylcyclotetrasiloxane comprising:

(a) reacting a dihalo-diphenylsilane having the formula, $(C_6H_5)_2Si(X)_2$ where X is a halogen selected from group consisting of Cl, Br, and I with an alcohol having the formula ROH where R is a monovalent hydrocarbon radical having from one to ten carbon atoms thereby producing a dialkoxydiphenylsilane having the formula $(C_6H_5)_2Si(OR)_2$ where R is as previously defined;

(b) mixing the dialkoxydiphenylsilane with a solvent wherein octaphenylcyclotetrasiloxane is sparingly soluble to form a mixture;

(c) adding thereto a base as a catalyst in an amount to provide a base concentration of about 1 to about 5,000 ppm and water to hydrolyze the dialkoxydiphenylsilane and (d) refluxing the mixture whereby octaphenylcyclotetrasiloxane precipitates from the solvent.

In addition the present invention also provides for a process for the production of sym-tetramethyltetraphenylcyclotetrasiloxane consisting essentially of:

(a) reacting a dihalomethylphenylsilane having the formula $(CH_3)(C_6H_5)Si(X)_2$ where X is a halogen selected from group consisting of Cl Br, and I with an alcohol having the formula ROH where R is a monovalent hydrocarbon radical having from one to ten carbon atoms thereby producing a dialkoxy-methylphenyl silane having the formula $(CH_3)(C_6H_5)Si(OR)_2$ where R is as previously defined;

(b) mixing the dialkoxy-methylphenyl silane with a solvent wherein sym-tetramethyltetraphenylcyclotetrasiloxane is sparingly soluble to form a mixture;

(c) adding thereto a base as a catalyst in an amount to provide a base concentration of 1 to 5,000 ppm and water to hydrolyze the dialkoxydiphenylsilane and (d) refluxing the mixture whereby sym-tetramethyltetraphenylcyclotetrasiloxane precipitates from the solvent.

DETAILED DESCRIPTION OF THE INVENTION

The present invention is based on the discovery that the use of selected organic solvents not only significantly improves the yield of the synthesis reactions but also controls the reaction to yield a specific cyclic siloxane, octaphenylcyclotetrasiloxane. The reaction is controlled by reason of the limited solubility of the desired product in the reaction solution. As the desired product is formed, the solubility of the product is rapidly exceeded due to the limited or sparing solubility of the product and thus product precipitates from solution. As product precipitates from solution the reaction equilibrium shifts due to the law of mass action to produce more product which upon exceeding the solubility of the product, precipitates.

The process of the present invention utilizes a diphenyldialkoxysilane (or methylphenyldialkoxysilane), typically prepared by the alcoholysis of a diphenyldihalogensilane. Thus the first step of the process is:

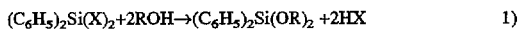

$$(C_6H_5)_2Si(X)_2 + 2ROH \rightarrow (C_6H_5)_2Si(OR)_2 + 2HX \quad 1)$$

where X is a halogen selected from group consisting of Cl, Br, and I and R is a monovalent hydrocarbon radical having from one to ten carbon atoms which may be aliphatic or aromatic in nature. While the reaction only requires 2 moles of alcohol on a stoichiometric basis, it is preferred to use an excess of the alcohol to drive off dissolved hydrohalic acid. The alcoholysis step, reaction 1) is followed by base catalyzed hydrolysis of the diphenyldialkoxysilane:

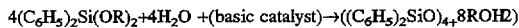

$$4(C_6H_5)_2Si(OR)_2 + 4H_2O + (basic\ catalyst) \rightarrow ((C_6H_5)_2SiO)_4 + 8ROH_2)$$

wherein the basic catalyst comprises an aqueous or aqueous alcoholic solution having a very low concentration of an alkali metal hydroxide, such as LiOH, NaOH, KOH, CsOH or RbOH or ammonium hydroxide, $NH_4OH$, typically on the order of about 100 ppm in the reaction mixture but which may range anywhere from about 1 ppm to about 5,000 ppm, preferably about 5 ppm to about 1,000 ppm, more preferably from about 5ppm to about 500 ppm, and most preferably from about 5 ppm to about 200 ppm. The reaction is conducted in the presence of sufficient water to perform the hydrolysis reaction. Generally preparation of an aqueous solution or an aqueous mixture comprising the base catalyst will provide sufficient water for the hydrolysis. A major advantage of the instant process is that when small amounts of base are used, e.g. from 5 to 200 ppm, this small amount need not be removed and can be left in the product as the melting point of the product is not significantly lowered. Thus, in contrast to the '070 patent no water washing is required. Since the reaction is a base catalyzed hydrolysis reaction, it is expected that other basic compounds known in the art might be employed to effect the hydrolysis of the diphenyldialkoxysilane. The hydrolysis reaction is conducted by boiling the reaction mixture at reflux conditions which is dependent upon the solvent or solvent mixture employed and is a function of the boiling points of the solvents used and their relative mole fractions. It should be noted that as alcohol is formed by the hydrolysis reaction, it will act as a co-solvent and will affect the reflux temperature as the reaction progresses. Another consequence of the change in solvent composition due to formation of product alcohol is that the solubility of the product octaphenylcyclotetrasiloxane will change somewhat because of the changing composition of the solvent mixture formed as a consequence of the reaction. In one embodiment a water miscible solvent is used in which the diphenyldialkoxysilane is soluble but in which the product, octaphenylcyclotetrasiloxane, is sparingly soluble or insoluble. Reaction 2) shows the re-formation of the alcohol, which should also be soluble in the solvent and which should not operate to substantially increase the solubility of the product octaphenylcyclotetrasiloxane. In general, oxygenated organic solvents work well to satisfy the reactant solubility—product insolubility requirement such solvents which are preferred are ketones, linear or cyclic ethers, esters and alcohols. Care must be employed when using alcohols as side reactions occur resulting in the formation of by-product alkoxy species. Thus it is preferred to utilize ketones and ethers or mixtures thereof either by themselves or in excess when used in conjunction with alcohols so that as product alcohol is formed from the diphenyldialkoxysilane in the course of the reaction, formation of by-product alkoxy species is minimized. Use of this type of solvent or solvent system typically precipitates most of the octaphenylcyclotetrasiloxane formed and thus the purity of the precipitated product is to a large extent dependent upon the purity of the starting diphenyldialkoxysilane compound. Thus it is preferred that the product octaphenylcyclotetrasiloxane have a solubility less than about 10 weight percent, preferably less than about 8 weight percent, more preferably less than about 6 weight percent and most preferably less than about 4 weight percent in the water miscible organic solvent or solvent mixture which is used to accomplish the reaction. Particularly preferred solvents are selected from the group consisting of acetone (dimethyl ketone), methyl iso-butyl ketone, methyl alcohol (methanol), ethanol, iso-propyl alcohol and ethyl acetate. Applicant hereby defines the term sparingly soluble to be a solubility of less than about 10 weight percent, preferably less than about 8 weight percent, more preferably less than about 6 weight percent and most preferably less than about 4 weight percent. One such solvent in which a particular diphenyldialkoxysilane is soluble, diphenyldimethoxysilane, is acetone. The product octaphenylcyclotetrasiloxane is sparingly soluble in acetone. Thus a particular embodiment of the process of the present invention hydrolyzes diphenyldimethoxysilane under conditions of base catalysis in acetone to yield octaphenylcyclotetrasiloxane which precipitates from the acetone methanol solution resulting from the hydrolysis in yields in excess of 90%.

In another embodiment of the invention a water miscible solvent or solvent mixture is not used. Instead a solvent mixture of toluene, hexane and methanol (formed from hydrolysis of the methoxysilane) is used to conduct the hydrolysis reaction which leads to the precipitation of the desired octaphenylcyclotetrasiloxane. Thus the process of the present invention comprises selecting a solvent or solvent mixture in which a given diphenyl dialkoxy silane is soluble but in which the hydrolysis product, octaphenylcyclotetrasiloxane, is sparingly soluble or insoluble, hydrolyzing the diphenyldialkoxysilane, and recovering the product octaphenylcyclotetrasiloxane.

The process of the present invention may also be used starting with dihalomethylphenylsilane, $(CH_3)(C_6H_5)Si(X)_2$, to produce sym-tetramethyltetraphenylcyclotetrasiloxane, $((CH_3)(C_6H_5)SiO)_4$.

All United States patents referenced herein are herewith and hereby specifically incorporated by reference.

EXPERIMENTAL

Experiment 1

100 parts by weight of diphenyldimethoxysilane containing no more than 0.2 weight percent phenyltrimethoxysilane was added to about 160 parts by weight acetone (200 parts by volume) to which was added water in an amount of 1.1 mole per mole of diphenyldimethoxysilane with sufficient NaOH to render a concentration of 100 ppm NaOH in the reaction mixture. The solution was heated to reflux for about five hours. Precipitation of the product octaphenylcyclotetrasiloxane was observed to begin about 40 minutes after reflux was initiated. The reaction mixture containing precipitated octaphenylcyclotetrasiloxane was cooled to room temperature, filtered and washed with acetone. The product was recovered in a 90% yield and had a melting point of 199° C.

The solubility of octaphenylcyclotetrasiloxane in some preferred solvents is as follows: acetone, 3.2 weight percent; methyl iso-butyl ketone, 1.9 weight percent, iso-propyl alcohol, 0.1 weight percent; and ethyl acetate, 3.6 weight percent.

Experiment 2

When experiment 1 is repeated with dihalomethylphenylsilane, sym-tetramethyltetraphenylcyclotetrasiloxane is produced. Addition of excess water increases the yield of sym-tetramethyltetraphenylcyclotetrasiloxane.

Having described the invention, that which is claimed is:

1. A process for the production of octaphenylcyclotetrasiloxane consisting essentially of:
  (a) reacting a dihalodiphenylsilane having the formula, $(C_6H_5)_2Si(X)_2$ where X is a halogen selected from group consisting of Cl, Br, and I with an alcohol having the formula ROH where R is a monovalent hydrocarbon radical having from one to ten carbon atoms thereby producing a dialkoxydiphenylsilane having the formula $(C_6H_5)_2Si(OR)_2$ where R is as previously defined;
  (b) mixing the dialkoxydiphenylsilane with a solvent wherein octaphenylcyclotetrasiloxane is sparingly soluble to form a mixture;
  (c) adding thereto a base as a catalyst in an amount to provide a base concentration of about 1 to about 5,000 ppm and water to hydrolyze the dialkoxydiphenylsilane and
  (d) refluxing the mixture whereby octaphenylcyclotetrasiloxane precipitates from the solvent.

2. The process of claim 1 wherein the solvent is an oxygenated organic solvent.

3. The process of claim 2 wherein the oxygenated solvent is selected from the group consisting of ketones, liner ethers, cyclic ethers, esters and alcohols.

4. The process of claim 3 wherein the oxygenated organic solvent is selected from the group consisting of acetone, methyl iso-butyl ketone, methanol, ethanol, iso-propyl alcohol and ethyl acetate.

5. The process of claim 4 wherein X is Cl.

6. The process of claim 5 wherein R is methyl.

7. The process of claim 6 wherein the base is selected from the group consisting of LiOH, NaOH, KOH, CsOH, RbOH and $NH_4OH$.

8. The process of claim 7 wherein the base is NaOH.

9. The process of claim 8 wherein the concentration of the base ranges from about 5 to about 200 ppm.

10. The process of claim 9 wherein the solvent is acetone.

11. A process for the production of sym-tetramethyltetraphenylcyclotetrasiloxane consisting essentially of:
  (a) reacting a dihalomethylphenylsilane having the formula $(CH_3)(C_6H_5)Si(X)_2$ where X is a halogen selected from group consisting of Cl, Br, and I with an alcohol having the formula ROH where R is a monovalent hydrocarbon radical having from one to ten carbon atoms thereby producing a methylphenyldialkoxysilane having the formula $(CH_3)(C_6H_5)Si(OR)_2$ where R is as previously defined;
  (b) mixing the dialkoxymethylphenylsilane with a solvent wherein sym-tetramethyltetraphenylcyclotetrasiloxane is sparingly soluble to form a mixture;
  (c) adding thereto a base as a catalyst in an amount to provide a base concentration of 1 to 5,000 ppm and water to hydrolyze the dialkoxydiphenylsilane and
  (d) refluxing the mixture whereby sym-tetramethyltetraphenylcyclotetrasiloxane precipitates from the solvent.

12. The process of claim 11 wherein the solvent is an oxygenated organic solvent.

13. The process of claim 12 wherein the oxygenated solvent is selected from the group consisting of ketones, liner ethers, cyclic ethers, esters and alcohols.

14. The process of claim 13 wherein the oxygenated organic solvent is selected from the group consisting of acetone, methyl iso-butyl ketone, methanol, ethanol, iso-propyl alcohol and ethyl acetate.

15. The process of claim 14 wherein X is Cl.

16. The process of claim 15 wherein R is methyl.

17. The process of claim 16 wherein the base is selected from the group consisting of LiOH, NaOH, KOH, CsOH, RbOH and $NH_4OH$.

18. The process of claim 17 wherein the base is NaOH.

19. The process of claim 19 wherein the concentration of the base ranges from about 5 to about 200 ppm.

20. The process of claim 19 wherein the solvent is acetone.

21. The process of claim 20 wherein the solvent is a mixture comprising acetone and water.

* * * * *

UNITED STATES PATENT AND TRADEMARK OFFICE
CERTIFICATE OF CORRECTION

PATENT NO. : 5,739,370
DATED : April 14, 1998
INVENTOR(S) : John S. Razzano

It is certified that error appears in the above-indentified patent and that said Letters Patent is hereby corrected as shown below:

On the title page, item [22] Filing Date should read:
--April 2, 1997 --

Signed and Sealed this

Eleventh Day of August 1998

*Attest:*

BRUCE LEHMAN

*Attesting Officer*     *Commissioner of Patents and Trademarks*